US011369270B2

(12) United States Patent
Ohbayashi et al.

(10) Patent No.: US 11,369,270 B2
(45) Date of Patent: Jun. 28, 2022

(54) METHOD OF EVALUATING THREE-DIMENSIONAL CELL-BASED STRUCTURE AND METHOD OF EVALUATING MEDICINAL EFFECT (71) Applicants: SCREEN HOLDINGS CO., LTD., Kyoto (JP); NATIONAL UNIVERSITY CORPORATION TOTTORI UNIVERSITY, Tottori (JP)

(72) Inventors: Tetsuya Ohbayashi, Tottori (JP); Yasushi Kuromi, Kyoto (JP); Masayoshi Kobayashi, Kyoto (JP)

(73) Assignees: SCREEN HOLDINGS CO., LTD., Kyoto (JP); NATIONAL UNIVERSITY CORPORATION TOTTORI UNIVERSITY, Tottori (JP)

( * ) Notice: Subject to any disclaimer, the term of this patent is extended or adjusted under 35 U.S.C. 154(b) by 536 days.

(21) Appl. No.: 16/467,906

(22) PCT Filed: Dec. 5, 2017

(86) PCT No.: PCT/JP2017/043657
§ 371 (c)(1),
(2) Date: Jun. 7, 2019

(87) PCT Pub. No.: WO2018/116818
PCT Pub. Date: Jun. 28, 2018

(65) Prior Publication Data
US 2020/0008680 A1 Jan. 9, 2020

(30) Foreign Application Priority Data
Dec. 20, 2016 (JP) .............................. JP2016-246254

(51) Int. Cl.
*A61B 5/00* (2006.01)
*C12N 5/071* (2010.01)
(Continued)

(52) U.S. Cl.
CPC .......... *A61B 5/0066* (2013.01); *A61B 5/0073* (2013.01); *C12N 5/0686* (2013.01);
(Continued)

(58) Field of Classification Search
CPC ... A61B 5/0066; A61B 5/0073; A61B 5/4848; C12M 41/46; C12N 2513/00;
(Continued)

(56) References Cited

U.S. PATENT DOCUMENTS

| 2012/0149110 A1 | 6/2012 | Kitamura et al. |
| 2016/0349240 A1 | 12/2016 | Fujimoto et al. |
| 2017/0358081 A1 | 12/2017 | Tsumura |

FOREIGN PATENT DOCUMENTS

| JP | 2004-275079 A | 10/2004 |
| JP | 2005-227097 A | 8/2005 |

(Continued)

OTHER PUBLICATIONS

Y. Jung et al., "Longitudinal, label-free, quantitative tracking of cell death and viability in a 3D tumor model with OCT", Scientific Reports, vol. 6, Article No. 27017, Jun. 1, 2016.
(Continued)

*Primary Examiner* — Mark D Remaly
(74) *Attorney, Agent, or Firm* — McDermott Will & Emery LLP (57) ABSTRACT

It is provided a technique capable of noninvasively and quantitatively evaluating the state of cultured three-dimensional cell-based structure. A method of evaluating a three-dimensional cell-based structure according to the present invention comprises: performing tomography of the cultured three-dimensional cell-based structure (step S103); generating stereoscopic data indicating the three-dimensional shape of the three-dimensional cell-based structure based on image data acquired by the tomography (step S104); and counting
(Continued)

the number of structures isolated from each other in the three-dimensional cell-based structure based on the stereoscopic data (step S105).

7 Claims, 7 Drawing Sheets

(51) Int. Cl.
*G01B 9/02091* (2022.01)
*G01N 33/50* (2006.01)

(52) U.S. Cl.
CPC ..... *G01B 9/02091* (2013.01); *G01N 33/5082* (2013.01); *C12N 2513/00* (2013.01)

(58) Field of Classification Search
CPC .............. C12N 5/0686; G01B 9/02044; G01B 9/02091; G01N 21/4795; G01N 33/5082
See application file for complete search history.

(56) References Cited

FOREIGN PATENT DOCUMENTS

| | | |
|---|---|---|
| JP | 2012-202761 A | 10/2012 |
| JP | 2014-093979 A | 5/2014 |
| WO | 2011/021558 A1 | 2/2011 |
| WO | 2015/141059 A1 | 9/2015 |
| WO | 2015/145872 A1 | 10/2015 |

OTHER PUBLICATIONS

Japanese Notice of Reasons for Refusal issued in corresponding Japanese Patent Application No. 2016-246254, dated Jul. 21, 2020, with English translation.

International Search Report issued in corresponding International Patent Application No. PCT/JP2017/043657, dated Mar. 13, 2018, with English translation.

Mizukami, T. et al., "Development of new screening and efficacy evaluation methods for anticancer agents based on three-dimensional (3D) shape measurement of spheroids using optical coherence tomography (OCT)," Biochemistry and Molecular Biology, Dec. 2, 2015, with English translation.

METHOD OF EVALUATING THREE-DIMENSIONAL CELL-BASED STRUCTURE AND METHOD OF EVALUATING MEDICINAL EFFECT

CROSS REFERENCE

This application is the U.S. National Phase under 35 US.C. § 371 of International Application No. PCT/JP2017/043657, filed on Dec. 5, 2017, which claims the benefit of Japanese Application No. 2016-246254, filed on Dec. 20, 2016, the entire contents of each are hereby incorporated by reference.

STATEMENT REGARDING PRIOR DISCLOSURES BY THE INVENTOR OR A JOINT INVENTOR

The following disclosure is submitted under 35 U.S.C. § 102(b)(1)(A): T. Ohbayashi, "In vivo nephrotoxicity assay using reconstituted 3-dimensional kidney-like structure," The 43rd Annual Meeting of the Japanese Society of Toxicology, Workshop 6, Jul. 1, 2016.

TECHNICAL FIELD

The present invention relates to an evaluation method of evaluating a cultured three-dimensional cell-based structure based on an image thereof, and a medicinal effect evaluation method of evaluating the medicinal effect of a chemical on the three-dimensional cell-based structure using the three-dimensional cell-based structure evaluation method. The "medicinal effect" mentioned in this description is a concept covering both favorable influence of a chemical on a biological body such as encouragement of breeding or improvement of a lesion, and adverse influence such as toxicity of damaging cells.

BACKGROUND ART

In the technical field of drug design of developing new medicines or the technical field of evaluating medicinal effect of examining influence of a chemical on a biological body, experiment is conducted for examining the influence of the chemical on the biological body. Known examples of such experiment include what is called in vivo test of administering a chemical to a biological body such as an animal and observing change, and what is called in vitro test of administering a chemical to a cell or a tissue cultured artificially in a container and observing the cell or tissue. Of these test, the in vitro test has advantages in terms of test cost, animal protection, etc. for not using a biological body for experiment. However, the in vivo test is still advantageous as it can determine influence of a chemical in a biological body in more detail.

In response to more activated studies on stem cells in recent years, knowledge about tissue differentiation has been accumulated. Further, tissue-like structures having configurations or functions artificially reproduced as those of various body parts or organs have been prepared (cell tissues or organoids, for example). Thus, knowledge in enough detail has been acquired even through the in vitro test.

There has been a technique of evaluating the state of a cultured three-dimensional cell-based structure quantitatively such as that described in Patent Literature 1, for example. According to this technique, a tissue to be observed is processed for convenience of observation by means of introduction of a marker or a reporter, and peculiar light emission resulting from such processes is measured. There has also been a different method of capturing an optical image of a cultured three-dimensional cell-based structure and analyzing the optical image by image processing as described in Patent Literature 2, for example.

CITATION LIST

Patent Literature

[Patent Literature 1] JP 2004-275079 A
[Patent Literature 2] WO 2011/021558 A1

SUMMARY OF INVENTION

Technical Problem

Degeneration of a three-dimensional cell-based structure is unavoidable in a method of processing a subject and observing the processed subject, or a method of slicing a subject and preparing a sample for capturing an image of the stereoscopic configuration of a three-dimensional cell-based structure. This makes it impossible to continuously evaluate temporal change in the three-dimensional cell-based structure. Further, the stereoscopic configuration of a stereoscopic three-dimensional cell-based structure cannot be expressed correctly in an image generated by projecting the three-dimensional cell-based structure on a two-dimensional image plane. In view of these aspects, the foregoing conventional techniques are susceptible to improvement.

By contrast to the foregoing techniques, a stereoscopic image of a three-dimensional cell-based structure may be captured noninvasively by a method using tomography technique such as optical coherent tomography (OCT), for example. This technique allows capturing of a clear stereoscopic image of a three-dimensional cell-based structure having a stereoscopic configuration. An image of a three-dimensional cell-based structure captured by this imaging technique is expected to be used in quantitative evaluation of the state of the three-dimensional cell-based structure. However, such an evaluation technique has not been established so far.

Solution to Problem

The present invention has been made in view of the foregoing problems. A first object of the present invention is to provide a technique allowing noninvasive and quantitative evaluation of the state of a cultured three-dimensional cell-based structure. A second object of the present invention is to provide a technique allowing noninvasive and quantitative evaluation of the medicinal effect of a chemical on a three-dimensional cell-based structure.

A first aspect of the present invention is a method of evaluating a three-dimensional cell-based structure. To fulfill the first object, the method comprises: performing tomography of a cultured three-dimensional cell-based structure; generating stereoscopic data indicating the three-dimensional shape of the three-dimensional cell-based structure based on image data acquired by the tomography; and counting the number of structures isolated from each other in the three-dimensional cell-based structure based on the stereoscopic data.

If a three-dimensional cell-based structure is cultured in environment favorable for living of cells, it is thought that the three-dimensional cell-based structure as a whole is maintained in a state of fulfilling a predetermined function. By contrast, if the three-dimensional cell-based structure is cultured in such environment as to debilitate cells, deterioration or death of cells leads to their loss of function. In this case, fragmentation of the three-dimensional cell-based structure is considered to progress in response to weakened connections between the cells. This means that determining whether a large number of cells forming the cultured three-dimensional cell-based structure are integrated or fragmented can be useful technique for determining the properness of culture environment or evaluating influence of a chemical added to the culture environment on cells.

According to the present invention, the number of isolated structures forming the cultured three-dimensional cell-based structure is counted based on data acquired by tomography of the three-dimensional cell-based structure. As the three-dimensional cell-based structure is fragmented further, the number of structures forming the three-dimensional cell-based structure and isolated from other structures increases. Thus, using a result of the count of such isolated structures makes it possible to express the state of the three-dimensional cell-based structure quantitatively.

In a two-dimensional image acquired by imaging of the three-dimensional cell-based structure having the stereoscopic configuration from a particular imaging direction, connections between the structures overlapping in the image cannot be grasped. Further, even if a sample including the three-dimensional cell-based structure is sliced into multiple layers and then images of the subject are captured, the connections between the structures in the corresponding layers may still be unclear. Further, the three-dimensional cell-based structure to be evaluated may be damaged.

By contrast, using stereoscopic data showing the three-dimensional shape of the three-dimensional cell-based structure acquired from a result of tomography makes it possible to identify a spatial region in space within an imaging range (imaging space) taken by the three-dimensional cell-based structure. Namely, the stereoscopic data can be used for grasping a range of the spatial region in the imaging space taken by one structure forming the three-dimensional cell-based structure. Thus, the stereoscopic data can also be used for determining the number of structures existing in the imaging space and isolated from each other.

As described above, the number of isolated structures in the three-dimensional cell-based structure is useful as an index for evaluating the state of the three-dimensional cell-based structure quantitatively. According to the present invention, the number of isolated structures in the three-dimensional cell-based structure counted based on the stereoscopic data acquired by tomography of the three-dimensional cell-based structure to be evaluated is used as an evaluation index for evaluating the three-dimensional cell-based structure. In this way, it becomes possible to evaluate the state of the cultured three-dimensional cell-based structure noninvasively and quantitatively.

Another aspect of the present invention is a medicinal effect evaluation method of evaluating the medicinal effect of a chemical. To fulfill the second object, the method comprises: administering the chemical to be evaluated to a cultured three-dimensional cell-based structure; evaluating the three-dimensional cell-based structure with the administered chemical using the foregoing method of evaluating the three-dimensional cell-based structure; and determining the medicinal effects of the chemical on the three-dimensional cell-based structure based on a result of the evaluation of the three-dimensional cell-based structure.

According to the invention having this configuration, the foregoing evaluation method is employed for evaluating the state of the three-dimensional cell-based structure with the administered chemical. By doing so, the state of the three-dimensional cell-based structure to be shown is quantified, so that the medicinal effect of the chemical can also be determined based on a quantitative criterion. Specifically, the present invention achieves noninvasive and quantitative evaluation of the medicinal effect of the chemical on the three-dimensional cell-based structure.

Advantageous Effects of Invention

In the method of evaluating the three-dimensional cell-based structure according to the present invention, the state of the three-dimensional cell-based structure is evaluated based on the number of isolated structures determined from stereoscopic data about the three-dimensional cell-based structure in a tomographic image. This makes it possible to evaluate the three-dimensional cell-based structure noninvasively and quantitatively. Further, in the medicinal effect evaluation method according to the present invention, a result of evaluation of a three-dimensional cell-based structure based on stereoscopic data acquired by tomography of the three-dimensional cell-based structure with the administered chemical is used for evaluating the medicinal effect of the chemical on the three-dimensional cell-based structure. This makes it possible to evaluate the medicinal effect noninvasively and quantitatively.

The foregoing objects and other objects, and new characteristics of the present invention will become more apparent completely by reading detailed description given below by referring to the accompanying drawings. The drawings are merely for explanation and are not intended to limit the scope of the invention.

DESCRIPTION OF EMBODIMENTS

The following describes a specific embodiment of a method of evaluating a three-dimensional cell-based structure and a method of evaluating the medicinal effect of a chemical according to the present invention. In the embodiment, a chemical such as a medicine to be evaluated is administered to a three-dimensional cell-based structure cultured in a container. Change in the three-dimensional cell-based structure with passage of time is observed to examine the medicinal effect of the chemical on the three-dimensional cell-based structure. The medicinal effect of the chemical is determined by considering some evaluation results comprehensively. In this embodiment, the medicinal effect is evaluated using the method of evaluating a three-dimensional cell-based structure according to the present invention as one method.

In the embodiment, the three-dimensional cell-based structure to become a target of determination of the medicinal effect of a chemical is cultured in advance in a culture medium poured in a transparent culture container having a flat bottom surface. A chemical to be evaluated is administered to the cultured three-dimensional cell-based structure. After passage of a predetermined length of time, a tomographic image of the three-dimensional cell-based structure is captured. Based on a result of analysis of the resultant tomographic image, the state of the three-dimensional cell-based structure is evaluated. Based on a result of the evaluation, the medicinal effect of the chemical on the three-dimensional cell-based structure is evaluated.

In a specific example of the embodiment described below, the present invention is applied to a toxicity test of evaluating the toxicity of a chemical to a kidney-like structure (corresponding to a "three-dimensional cell-based structure") prepared by culture from stem cells of a rat kidney. However, this is not the limitations in terms of the type of a three-dimensional cell-based structure to be evaluated according to the present invention, purpose of the evaluation, etc.

The configuration of an image processing apparatus for capturing a tomographic image and the principles of imaging by the image processing apparatus will be described first. Then, a method of evaluating the state of a three-dimensional cell-based structure and a method of evaluating the medicinal effect of a chemical using data acquired by the imaging will be described.

Figure 1:
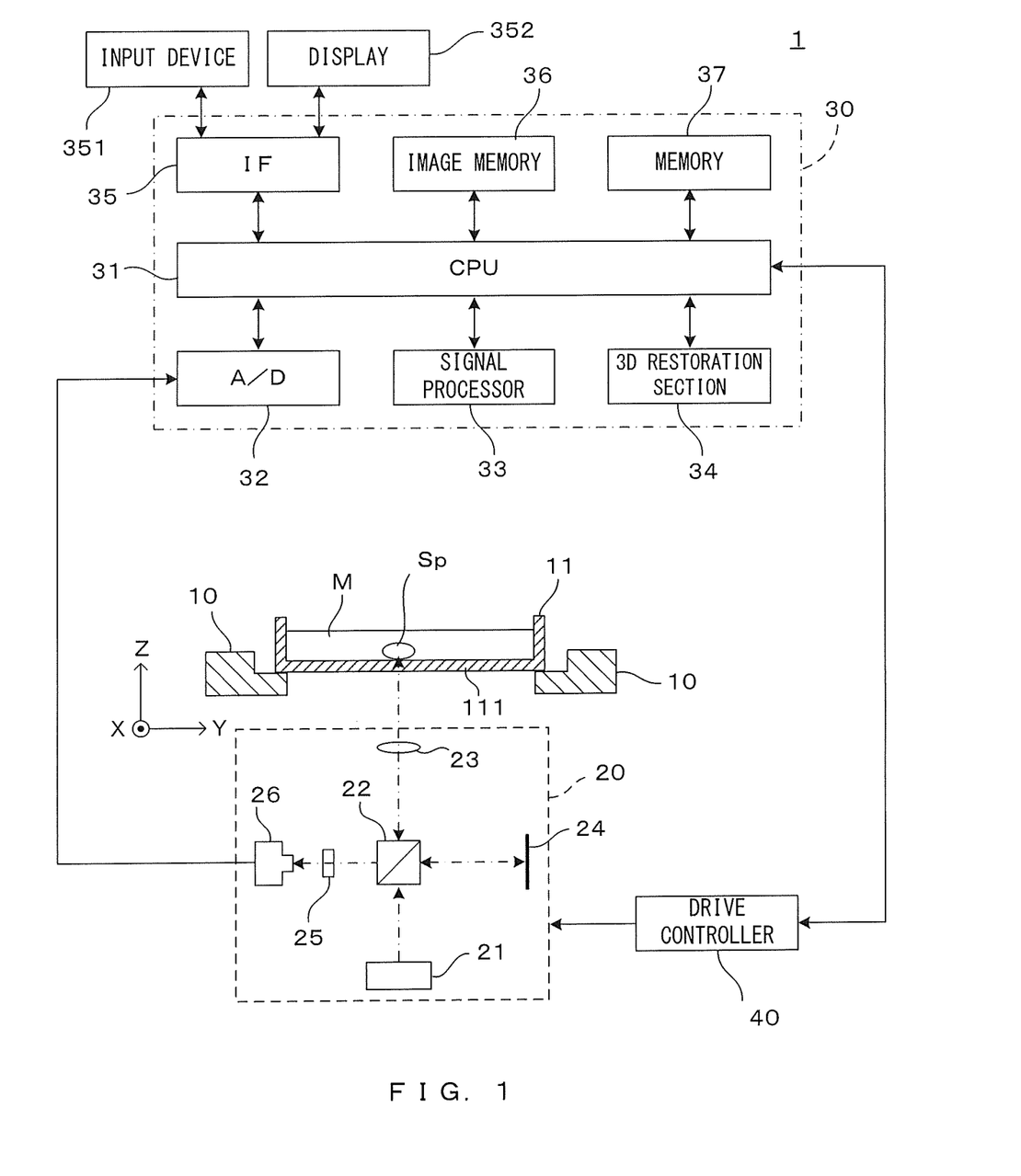
FIG. 1 is a drawing showing the image processing apparatus for obtaining tomographic images.

FIG. 1 is a drawing showing the image processing apparatus for obtaining tomographic images. The image processing apparatus 1 tomographically images various types of specimens such as a cell, cell aggregate or the like cultured in culture medium as an imaging object, processes the obtained image and generates a stereoscopic image of the spheroid. Note that although an example of imaging a specimen of three-dimensional cell-based structures cultured in culture medium injected into an appropriate culture container as the imaging object is described here, the imaging object is not limited to this. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The image processing apparatus 1 comprises a holder 10. The holder 10 holds in an approximately horizontal posture a container 11 in such a manner that an opening thereof is directed toward above. The container 11 is a device called a shallow dish having a flat bottom surface made of transparent and uniform glass or resin. A predetermined amount of an appropriate culture medium M is poured in the container 11 in advance, and a specimen Sp is cultured in the medium at the bottom part 111 of the container 11. Although FIG. 1 shows only one specimen Sp, a plurality of specimens Sp may be cultured in one container 11.

An imaging unit 20 is disposed below the container 11 which is held by the holder 10. An optical coherence tomography (OCT) apparatus capable of imaging tomographic images of an imaging object in a non-contact non-destructive (non-invasive) manner is used as the imaging unit 20. The imaging unit 20 which is an OCT apparatus comprises a light source 21 which emits illumination light for an imaging object, a beam splitter 22, an objective optical system 23, a reference mirror 24, a spectroscope 25 and a photo-detector 26.

Further, the image processing apparatus 1 comprises a control unit 30 which controls operations of the apparatus and a drive controller 40 which controls movement of movable parts of the imaging unit 20. The control unit 30 comprises a CPU (Central Processing Unit) 31, an A/D converter 32, a signal processor 33, a 3D restoration section 34, an interface (IF) section 35, an image memory 36, a memory 37 and the like.

The CPU 31 governs operations of the entire apparatus by executing a predetermined control program. The control program executed by the CPU 31 and data which are generated during processing are saved in the memory 37. The A/D converter 32 converts a signal which the photo-detector 26 of the imaging unit 20 outputs in accordance with the amount of received light into digital image data. The signal processor 33 performs appropriate image processing based upon a digital data outputted from the A/D converter 32, thereby generates a tomographic image of the imaging object. Based upon image data of a plurality of tomographic images, the 3D restoration section 34 generates a stereoscopic image (3D image) of the imaged cell aggregate. The image memory 36 saves the image data of the tomographic images generated by the signal processor 33 and the image data of the stereoscopic image generated by the 3D restoration section 34.

The interface section 35 realizes communication between the image processing apparatus 1 and outside. More specifically, the interface section 35 has a function of communicating with external equipment, and a user interface function of accepting manipulation by a user and informing the user of various types of information. For this purpose, an input device 351 and a display section 352 are connected to the interface section 35. The input device 351 is for instance a key board, a mouse, a touch panel or the like which can accept manipulation and entry concerning selection of the functions of the apparatus, setting of operating conditions, etc. The display section 352 comprises a liquid crystal display for example which shows various types of processing results such as the tomographic images imaged by the imaging unit 20 and the stereoscopic image generated by the 3D restoration section 34.

Further, the drive controller 40 makes the imaging unit 20 scan and move in accordance with a control command given from the CPU 31. As described next, the tomographic images of the three-dimensional cell-based structures to be imaged are obtained owing to combination of scan moving of the imaging unit 20 executed by the drive controller 40 and detection of the amount of the received light by the photo-detector 26.

Figure 2A:
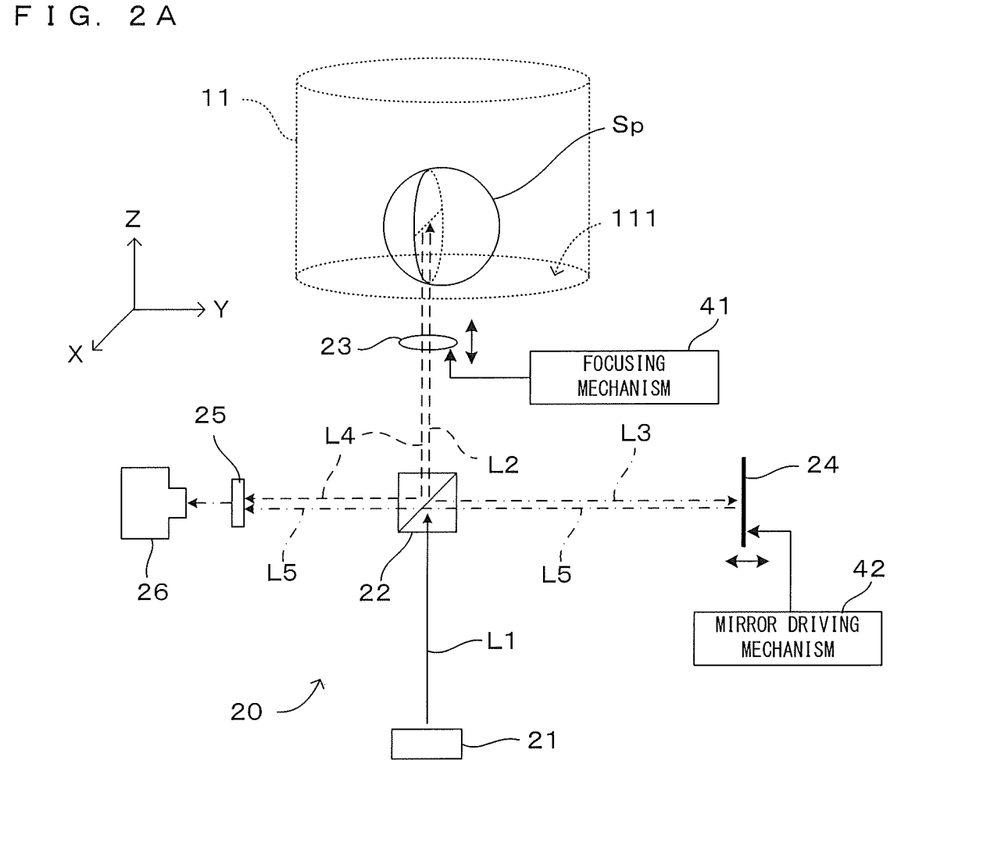
FIGS. 2A and 2B are drawings for describing the principle of imaging in the image processing apparatus.
Figure 2B:
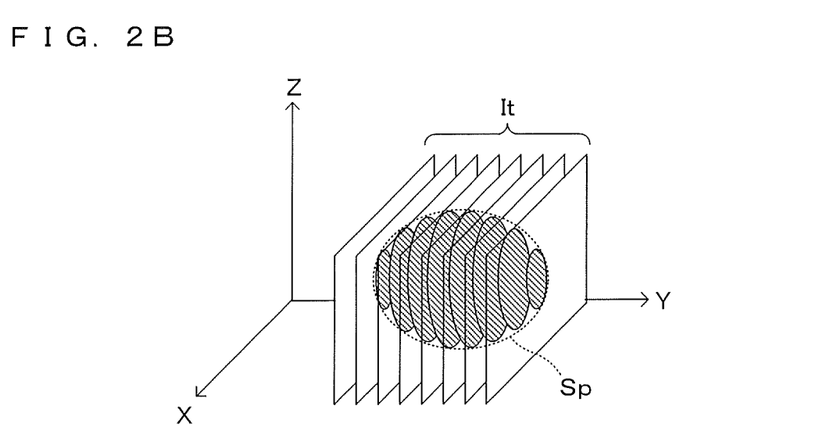

FIGS. 2A and 2B are drawings for describing the principle of imaging in this image processing apparatus. More specifically, FIG. 2A is a drawing which shows optical paths inside the imaging unit 20, and FIG. 2B is a schematic drawing which shows tomographic imaging of the specimen Sp. As described earlier, the imaging unit 20 works as an optical coherence tomography (OCT) apparatus. In addition, although the specimen Sp is displayed in a substantially spherical shape for description here, in the actual imaging, the shape of the specimen Sp is not specifically limited. For example, as described later, a kidney-like structure differentiated and cultured from stem cells has a complex structure which is branched into various parts.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22, and some light L2 indicated by the broken-line arrow propagates toward the well W, and some light L3 indicated by the arrow of long dashed short dashed line propagates toward the reference mirror 24.

The light L2 propagating toward the well W is incident on the container 11 by way of the objective optical system 23. More specifically, the light L2 emitted from the beam splitter 22 is incident on the bottom part 111 of the container 11 via the objective optical system 23. The objective optical system 23 has a function of converging the light L2 propagating from the beam splitter 22 toward the container 11 to the specimen Sp in the container 11 and a function of collecting the reflected light emitted from the specimen Sp and causing it to propagate toward the beam splitter 22. Although the objective optical system 23 is illustrated as a single objective lens in FIG. 2A, the objective optical system 23 may include a plurality of optical elements.

The objective optical system 23 is movable in the Z direction by a focusing mechanism 41 which is disposed to the drive controller 40. This enables the focus position of the objective optical system 23 with respect to the imaging object to be changed in the Z direction. An optical axis of the objective optical system 23 is parallel to a vertical direction and, therefore, perpendicular to the bottom part 111 of the container 11 in the form of a flat surface. Further, an incident direction of illumination light on the objective optical system 23 is parallel to the optical axis, and the arrangement of the objective optical system 23 is determined such that a light center of the light coincides with the optical axis.

The incident light L2 via the bottom part 111 is reflected at the surface of the specimen Sp unless the specimen Sp transmits the light beam L2. On the other hand, when the specimen Sp has a property of transmitting the light beam L2 to a certain extent, the light beam L2 propagates into inside the specimen Sp and is reflected by a structure element which is inside the spheroid. When the near infrared rays for instance are used as the light beam L2, it is possible to allow the incident light to reach even inside the specimen Sp. The reflected light from the specimen Sp is irradiated as scattered light in various directions. Out of that, light L4 irradiated within a light collection range of the objective optical system 27 is collected by the objective optical system 27 and sent to the beam splitter 22.

The reference mirror 24 is movably supported by a mirror driving mechanism 42 provided in the drive controller 40. Thus, the reference mirror 24 is able to move in a direction (Y direction in FIG. 2A) along the incident direction while a reflection surface thereof is perpendicular to an incident direction of the light L3. The light L3 incident on the reference mirror 24 is reflected by the reflection surface and propagates toward the beam splitter 22 as light L5 propagating in an opposite direction along an incident optical path. This light L5 becomes reference light. By changing the position of the reference mirror 24 by the mirror driving mechanism 42, an optical path length of the reference light changes.

The reflected light L4 reflected by a surface or an internal reflecting surface of the specimen Sp and reference light L5 reflected by the reference mirror 24 are incident on the photo-detector 26 via the beam splitter 22. At this time, interference light due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of the embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier-transforming the interference signal output from the photo-detector 26 according to the interference light detected by the photo-detector 26, the reflected light intensity distribution of the specimen Sp in the depth direction, i.e. in the Z direction at the incident position of the light beam L2 is obtained. By scanning the light beam L2 incident on the container 11 in the X direction, the reflected light intensity distribution in a plane parallel to an XZ plane is obtained, with the result that a tomographic image of the specimen Sp having this plane as a cross-section can be generated. In this specification, a series of operations for obtaining one tomographic image It in a cross-section parallel to the XZ plane by beam scanning in the X direction is referred to as one imaging.

While changing the beam incident position in the Y direction in multiple steps, imaging of a tomographic image is performed each time. As shown in FIG. 2B, a number of tomographic images It of the specimen Sp are obtained along cross-sectional surfaces which are parallel to the XZ plane. As the scan pitch in the Y direction is reduced, it is possible to obtain image data with sufficient resolution to grasp the stereoscopic structure of the specimen Sp. As indicated by the dotted-line arrow, the relative position of the imaging unit 20 to the well W is changed along the Y direction over multiple steps, and a tomographic image is imaged for every change. Scan movements of the light beam in X and Y direction are realized as an optical device (not shown) changing an optical path such as a Galvanometer mirror changes the incident position of the light beam to X and Y direction, the container 11 carrying the specimen Sp and imaging unit 20 relatively move to X and Y direction or the like.

Note that, in the imaging unit 20 of the above description, it is the beam splitter 22 that has a function of dividing the light from the light source 21 to the illumination light and the reference light and a function of mixing the signal light and the reference light to cause interference. On the other hand, some of OCT imaging apparatuses are known to have a dividing/mixing function, for example, an optical fiber coupler besides such a beam splitter as one of various optical devices capable of branching and mixing light waves.

Figure 3A:
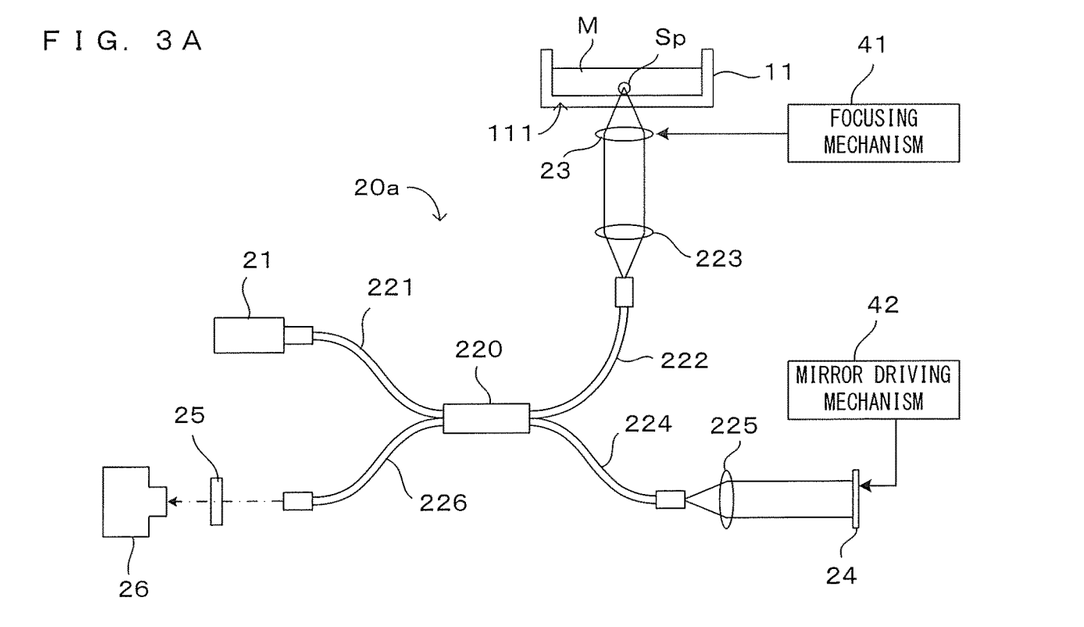
FIGS. 3A and 3B are diagrams showing other configuration examples of the OCT apparatus.
Figure 3B:
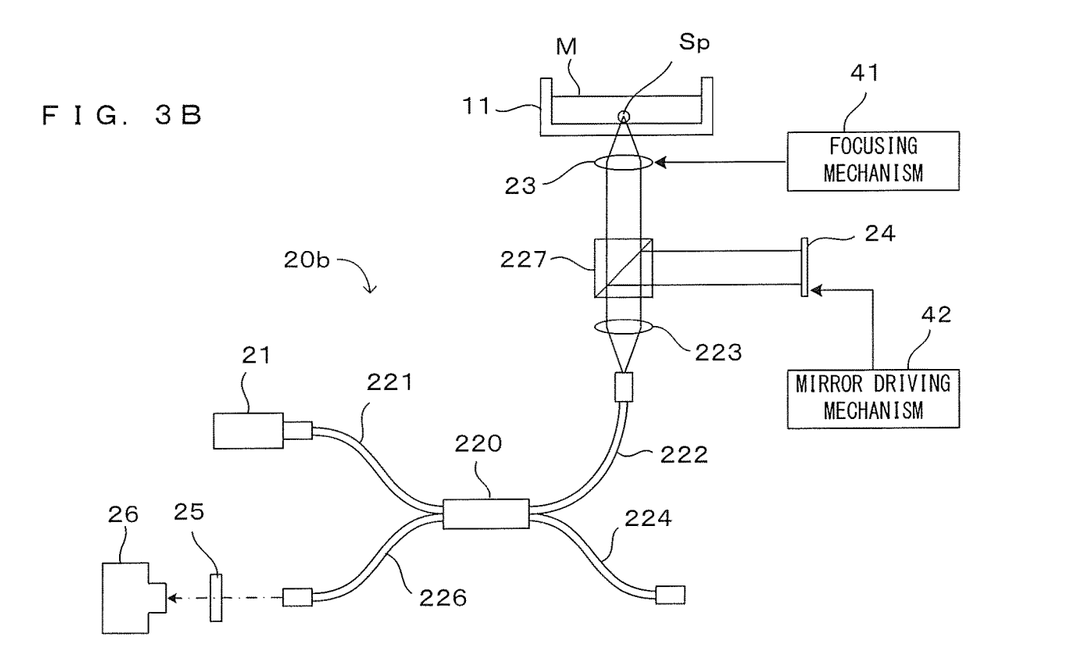

FIGS. 3A and 3B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted. An OCT imaging principle for detecting interference light by the optical fiber coupler is not described in detail since it is known.

In an example shown in FIG. 3A, an imaging unit 20a includes an optical fiber coupler 220 instead of the beam splitter 22 as an optical device. One optical fiber 221 constituting the optical fiber coupler 220 is connected to a light source 21 and low-coherence light emitted from the light source 21 is branched into lights to two optical fibers 222, 224 by the optical fiber coupler 220. The optical fiber 222 constitutes an object side optical path. More specifically, light emitted from an end part of the optical fiber 222 is incident on an objective optical system 23 via a collimator lens 223. Reflected light (signal light) from an imaging object is incident on the optical fiber 222 via the objective optical system 23 and the collimator lens 223.

Another optical fiber 224 constitutes a reference side optical path. More specifically, light emitted from an end part of the optical fiber 224 is incident on a reference mirror 24 via a collimator lens 225. Reflected light (reference light) from the reference mirror 24 is incident on the optical fiber 224 via the collimator lens 225. The signal light propagating in the optical fiber 222 and the reference light propagating in the optical fiber 224 interfere in the optical fiber coupler 220. Interference light is incident on a photo-detector 26 via an optical fiber 226 and a spectroscope 25. An intensity distribution of the reflected light on the imaging object is obtained from the interference light received from the photo-detector 26 as in the above embodiment.

Also in an example shown in FIG. 3B, an optical fiber coupler 220 is provided in an imaging unit 20b. However, an optical fiber 224 is not used and a collimator lens 223 and a beam splitter 227 are provided on an optical path of light emitted from an optical fiber 222. As in the embodiment described above, an objective optical system 23 and a reference mirror 24 are arranged on two optical paths branched by the beam splitter 227. In such a configuration, signal light and reference light are mixed by the beam splitter 227 and interference light generated thereby is guided to a photo-detector 26 through the optical fibers 222, 226.

In these examples, the optical path of each light propagating in a space is partially replaced by an optical fiber in the principle diagram of FIG. 2A, but the operation principle is the same. Also in these examples, the focusing mechanism 41 moves the objective optical system 23 in directions toward and away from the container 11. Thereby, it is possible to adjust the focal depth of the objective optical system 23 with respect to the object to be imaged. Further, the mirror driving mechanism 42 moves the reference mirror 24 along the incident direction of the light. Thereby, the optical path length of the reference light can be changed.

The following describes a method of a toxicity test conducted using the image processing apparatus 1 in detail. Both a configuration using the foregoing beam splitter and a configuration using the foregoing optical fiber coupler are applicable to the image processing apparatus 1. An imaging device for capturing a tomographic image is not limited to the foregoing FD-OCT imaging device. For example, an imaging device based on other imaging principles such as a time-domain OCT (TD-OCT) imaging device is also applicable.

The following processing is performed by execution of the control program stored in advance in the memory 37 by the CPU 31 of the image processing apparatus 1. However, this is not the only way of the implementation. In an alternative configuration, a computer different from the image processing apparatus 1 may receive OCT imaging data from the image processing apparatus 1 and may perform processing including step S104 and subsequent steps in FIG. 4, for example. This allows the CPU 31 of the image processing apparatus 1 to be responsible only for processing specialized for imaging to reduce processing load on the CPU 31.

Figure 4:
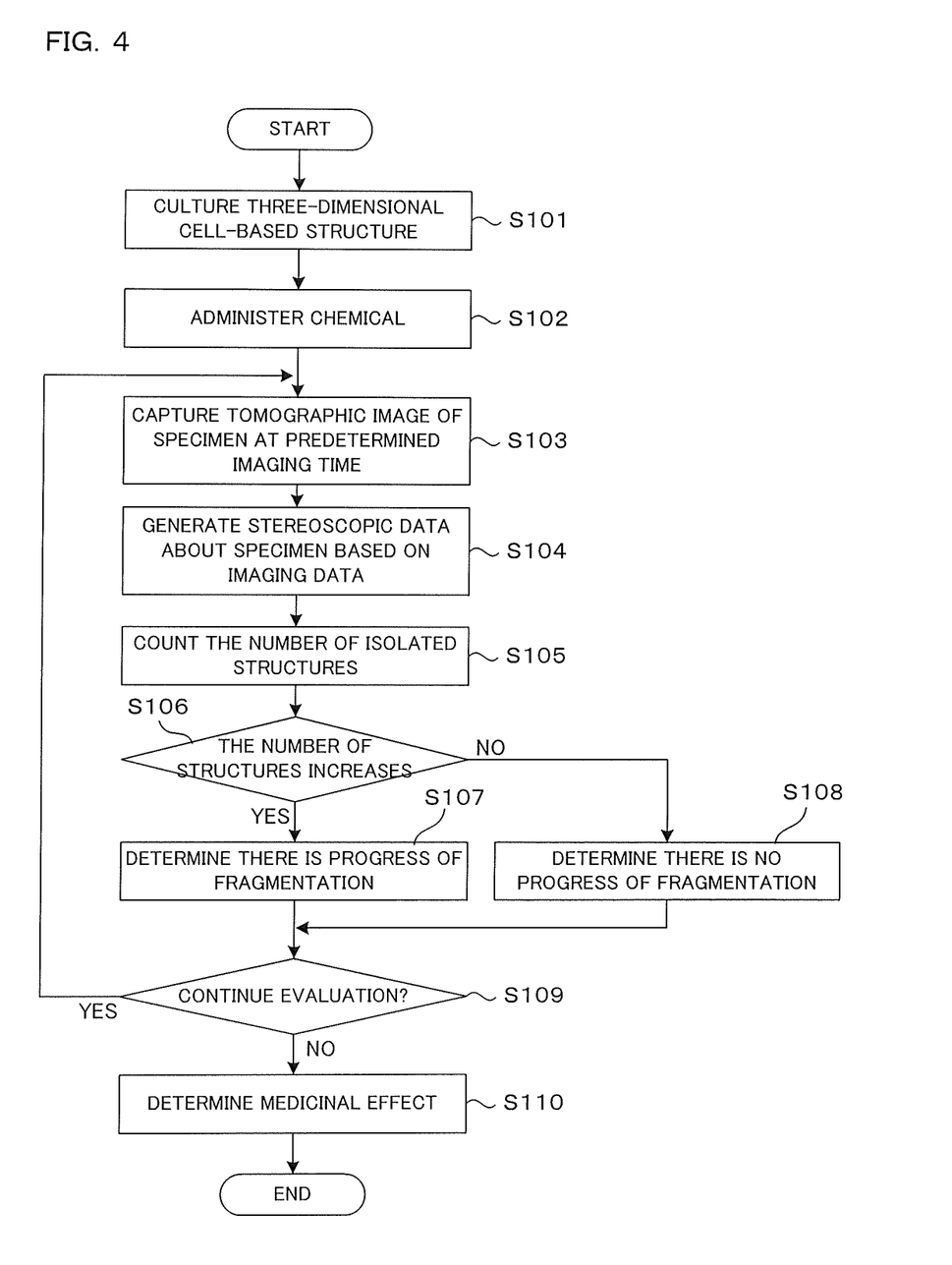
FIG. 4 is a flowchart showing the processing details of the toxicity test according to the embodiment.

FIG. 4 is a flowchart showing the processing details of the toxicity test according to the embodiment. In the toxicity test, a three-dimensional cell-based structure to be subjected to the toxicity test is first cultured in an appropriate container (step S101). For example, the three-dimensional cell-based structure may be a kidney-like structure differentiated from rat kidney-deriver stem cells and cultured. A three-dimensional cell-based structure having a three-dimensional configuration approximate to a shape in a biological body can be prepared by culture using hanging drop technique, for example.

A chemical of a predetermined dose to be evaluated in terms of toxicity is administered to the three-dimensional cell-based structure cultured in this way, thereby preparing a specimen Sp (step S102). Time after passage of a predetermined length of time from the administration is set as imaging time. When the imaging time has come, the image processing apparatus 1 captures a tomographic image of the specimen Sp (step S103). As will be described later, several imaging times are settable.

As described above, as a result of one imaging, imaging data about a tomographic image of the specimen Sp taken in a cross section parallel to the XZ plane is acquired. By performing imaging several times while changing an imaging position in the Y direction, imaging data corresponding to a stereoscopic image indicating the three-dimensional configuration of the specimen SP is acquired.

With the same imaging position in the Y direction, imaging may be performed several times with a focal position of the objective optical system 23 differing in the Z direction. In the FD-OCT imaging, a detected spectrum contains information about an imaging subject in a depth direction, and information about a certain range in the depth direction can be acquired by one imaging. Meanwhile, performing imaging several times at different positions in the depth direction makes it possible to reduce a range in the depth direction to be covered by one imaging. Thus, image resolution can be improved by using the objective optical system 23 having a large numerical aperture (NA), for example. A high-resolution tomographic image having a wide imaging rage in the depth direction can be acquired by combining tomographic images resulting from imaging performed several times.

Each tomographic image shows the configuration of the specimen Sp taken at one cross section parallel to the XZ plane. As a result of image processing performed by employing an appropriate interpolation method by the signal processor 33 and the 3D reconstruction section 34, interpolation in the Y direction is applied between multiple tomographic images resulting from imaging at positions differing in the Y direction. By doing so, stereoscopic data corresponding to a three-dimensional image (stereoscopic image) of the specimen Sp is generated (step S104). The stereoscopic image can be presented to a user by being output on the display 352, for example.

Figure 5:
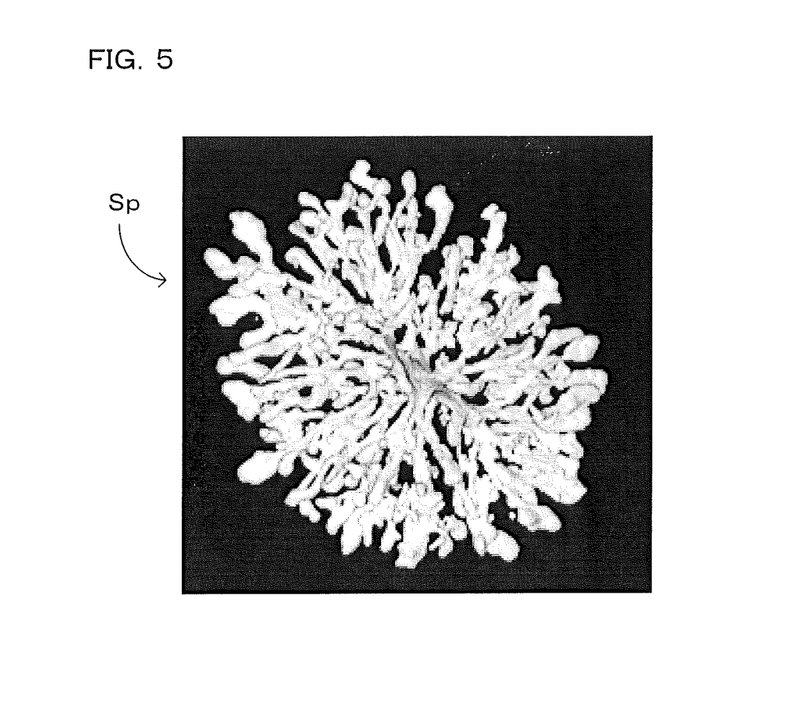
FIG. 5 shows an example of a stereoscopic image acquired from a tomographic image.

FIG. 5 shows an example of a stereoscopic image acquired from a tomographic image. A stereoscopic image of the specimen Sp acquired from tomographic images resulting from imaging performed several times can be displayed on a display screen on a computer through use of appropriate 3D viewer software. The exemplary image in FIG. 5 shows a kidney-like structure cultured from stem cells in a culture medium. As shown in FIG. 5, the cultured kidney-like structure has a shape with a large number of branching arms extending externally radially from a center.

In this case, the displayed image of a specimen has a shape determined by projecting the specimen as a stereoscopic structure viewed from a certain eye direction on a two-dimensional plane. Hence, if structures on the front and on the back overlap each other in this eye direction, the structure on the back is shielded by the structure on the front. In this regard, as the stereoscopic data is generated from imaging data acquired by tomography performed several times, an image of the specimen Sp viewed from any eye direction can be displayed by the use of a 3D viewer. This makes it possible to determine visually whether structures overlapping each other in an image are continuous or isolated from each other.

As described above, a stereoscopic configuration of the specimen Sp as a three-dimensional cell-based structure can be identified based on imaging data acquired by tomography, and the identified stereoscopic configuration can be output for display as a stereoscopic image, for example. This allows a user to check the shape of the three-dimensional cell-based structure to be observed on the screen. By doing so, it becomes possible for the user to determine qualitatively whether the three-dimensional cell-based structure is in an active state or a debilitated state.

However, in the evaluation by this observer's subjective determination, the evaluation result tends to be influenced by the skill level of the observer. Additionally, it is difficult to compare multiple specimens having respective different shapes. In this regard, it is desirable to introduce an index that objectively and quantitatively represents the state of the three-dimensional cell-based structure in a captured image. An index preferably used for such purpose can be determined using stereoscopic data generated from an imaging result acquired by OCT tomography. An example of this idea will be described next.

The configuration of a three-dimensional cell-based structure contained in space within an imaging range covered by imaging performed several times (hereinafter called "imaging space") can be determined by appropriate image analysis processing. For example, if the imaging space includes a point that can be assumable belonging to a surface of a structure in the three-dimensional cell-based structure based on the brightness level thereof, the contour of this structure can be identified by sequentially searching for points having spatial connectivity with respect to the point. Publicly-known image processing such as region-dividing process is applicable to this search. As a result of this image processing, a spatial region surrounded by a single closed surface having spatial connectivity in the imaging space is identified as an object corresponding to one structure. Structures without spatial connectivity and isolated from each other (hereinafter may also be called "isolated structures") are considered to be different objects.

The shape of a three-dimensional cell-based structure having a stereoscopic configuration can be expressed as numerical data by means of 3D modeling processing using appropriate image editing software. The surface of the three-dimensional cell-based structure may be expressed approximately as an aggregate of tiny polygons, for example. A method using triangular meshes is applicable, for example. According to such a method of expression, the surface of the structure contained in a stereoscopic image and having spatial connectivity is expressed as an aggregate of polygons. In other words, the shape of one structure is identified using polygon data generated by gathering coordinate information about corresponding polygons that represent a surface of the structure approximately.

As described above, based on image data acquired by OCT tomography, stereoscopic data (polygon data, for example) can be generated by forming a 3D model of each structure in the three-dimensional cell-based structure. Thus, after the generation, an image of the three-dimensional cell-based structure viewed from any direction can be displayed on a display screen. For example, the image can be rotated on the screen, if necessary.

Such stereoscopic data can be used for calculating various types of index values indicating the features of the shape of each structure in a three-dimensional cell-based structure such as the approximate values of the surface area and volume of this structure. The number of objects identified in the stereoscopic data indicates the number of structures forming the three-dimensional cell-based structure. These index values can also be used as indexes for evaluating the state of the three-dimensional cell-based structure quantitatively.

More specifically, if the three-dimensional cell-based structure in a captured image is highly active, the surface area and volume of this three-dimensional cell-based structure are considered to be larger than those of a debilitated three-dimensional cell-based structure having a substantially equal size expressed by an envelope volume, for example. Meanwhile, the number of isolated structures forming the three-dimensional cell-based structure is considered to increase as the three-dimensional cell-based structure is debilitated more seriously. The reason for this is as follows. In the three-dimensional cell-based structure in which a large number of cells are connected organically to fulfill a certain function, having high activity does not cause increase in isolated structures. Typically, the three-dimensional cell-based structure with a high organization is composed of a single structure. By contrast, if cells forming the three-dimensional cell-based structure become debilitated, interconnections between the cells are weakened to facilitate fragmentation of the tissue. This is considered to cause increase in the number of isolated structures.

In particular, OCT tomography achieves noninvasive imaging not causing damage on the specimen Sp. In view of this, change in the state of the three-dimensional cell-based structure can be observed continuously by imaging the same specimen Sp several times at time intervals. This achieves temporal evaluation of change in the three-dimensional cell-based structure in particular environment, for example, while the three-dimensional cell-based structure has an administered chemical.

This functions largely advantageously in a test of the toxicity of a chemical to the three-dimensional cell-based structure. If the chemical administered to the three-dimensional cell-based structure has toxicity of causing disorder in cells, for example, collapse of the three-dimensional cell-based structure progresses with time. In this case, the number of isolated structures in the three-dimensional cell-based structure grasped from stereoscopic data is considered to increase gradually with time. More specifically, if the number of isolated structures forming the three-dimensional cell-based structure increases in response to administration of the chemical, the chemical can be determined to have toxicity to the three-dimensional cell-based structure.

When a stereoscopic object is projected on a two-dimensional plane and displayed on a display screen, structures originally isolated from each other overlap each other in an image. Hence, in some cases, it becomes difficult to determine whether these structures are integrated or isolated from each other. Even if an image of the three-dimensional cell-based structure viewed from an intended eye direction can be displayed, it is still difficult to grasp the number of isolated structures in the displayed image. By contrast, stereoscopic data generated based on OCT tomography makes it possible to separate individual isolated structures from each other as spatial regions each surrounded by a closed surface having spatial connectivity. In this way, the number of isolated structures in the three-dimensional cell-based structure can be counted reliably.

The description of the toxicity test will be described continuously by referring back to FIG. 4. The toxicity of the chemical is evaluated based on the stereoscopic data generated from the result of OCT tomography and the foregoing principles. More specifically, the number of isolated structures in the specimen Sp is counted using the stereoscopic data generated in step S104 (step S105). At this time, as will be described later, the volume and surface area of the three-dimensional cell-based structure may be determined together based on the stereoscopic data.

If the number of isolated structures at some point in time in the past (before administration of the chemical, for example) is known in advance about the same specimen Sp, a current result of the count newly acquired and the previous number are compared to evaluate the state of the three-dimensional cell-based structure. More specifically, if the number of isolated structures increases significantly (if YES in step S106), the three-dimensional cell-based structure is determined to be fragmented further (step S107). If no significant increase is recognize in the number of isolated structures (if NO in step S106), it is determined that fragmentation does not progress in the three-dimensional cell-based structure (step S108).

If the specimen Sp is required to be observed and evaluated continuously (if YES in step S109), the flow returns to step S103. If next imaging time has come, OCT tomography is performed again for implementation of processing in the same way as the foregoing.

If OCT imaging and evaluation of the three-dimensional cell-based structure based on the OCT imaging are finished completely (if NO in step S109), the presence or absence of the toxicity of the chemical to be evaluated is determined conclusively (step S110). More specifically, if administration of the chemical is determined to fragment the three-dimensional cell-based structure further, the chemical is determined to have toxicity to this three-dimensional cell-based structure. If no significant fragmentation is recognized in the three-dimensional cell-based structure, the chemical is determined not to have toxicity to this three-dimensional cell-based structure.

A further evaluation criterion in addition to the foregoing may be defined for making determination as to the presence or absence of toxicity. As described above, for example, the surface area or volume of the three-dimensional cell-based structure can also be an index value indicating the state of the three-dimensional cell-based structure. If the three-dimensional cell-based structure includes multiple isolated structures, a total of the surface areas or volumes of these isolated structures is used as an index value. Further, one sample may be evaluated more than once at different times, and the toxicity of the chemical can be evaluated based on temporal change in the state of the three-dimensional cell-based structure. Additionally, toxicity may be determined comprehensively based on evaluation results about multiple samples to which administrations of different doses (concentrations) have been given.

Figure 6A:
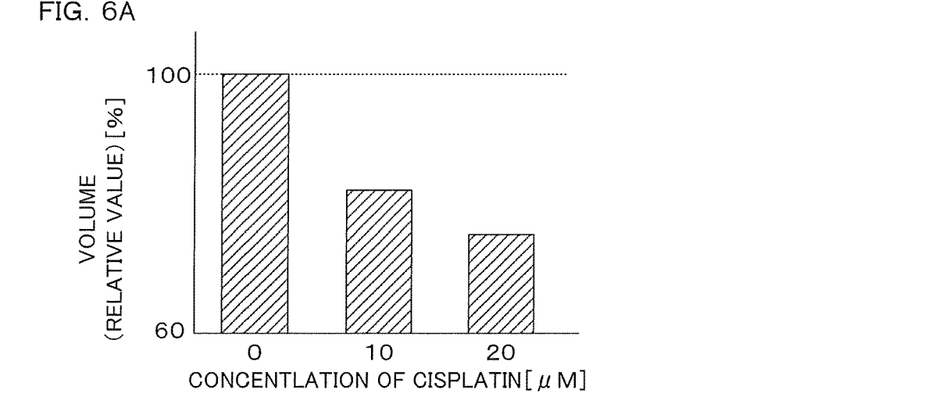
FIGS. 6A to 6C show examples of results of the toxicity test.
Figure 6B:
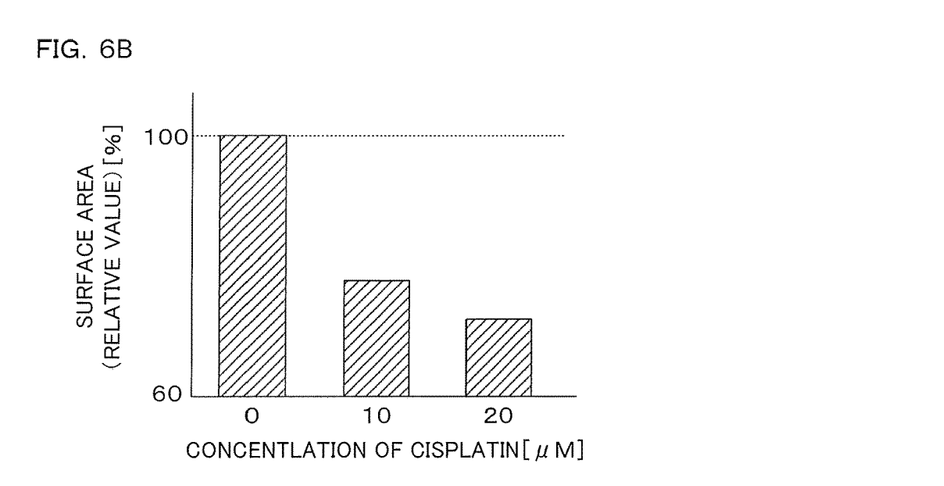
Figure 6C:
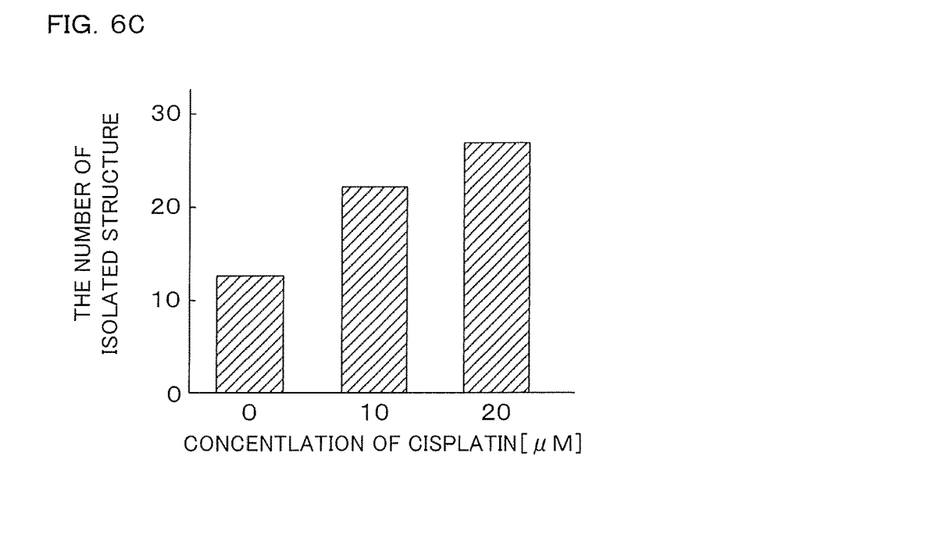

FIGS. 6A to 6C show examples of results of the toxicity test. To verity the foregoing test method, the applicant of the present application conducted the following experiment. In the experiment, cisplatin (CisPt) known as a nephrotoxic material was administered to a cultured kidney-like structure as an example of a three-dimensional cell-based structure, and toxicity was quantitatively evaluated using an index value acquired by OCT imaging. More specifically, samples were prepared by adding cisplatin of various concentrations to kidney-like structures prepared by differentiation from stem cells derived from a rat kidney and culture. After passage of a predetermined length of time from the administrations, the specimens were subjected to OCT imaging, and the respective surface areas and volumes of the three-dimensional cell-based structures, and the respective numbers of isolated structures in these three-dimensional cell-based structures were calculated as index values from stereoscopic data resulting from the OCT imaging. Multiple specimens at corresponding concentrations were prepared. An index value is an average of values about these specimens. FIGS. 6A and 6B are graphs each showing a relationship between the concentration of administered cisplatin and an index value.

FIG. 6A shows a relationship between a cisplatin concentration and the volume of the three-dimensional cell-based structure. FIG. 6B shows a relationship between a cisplatin concentration and the surface area of the three-dimensional cell-based structure. The volume and surface area are values relative to corresponding values in a group without administered cisplatin. In a group with administered cisplatin, significant reduction is recognized in the relative volume and the relative surface area compared to the group without administered cisplatin. Reduction becomes more notable with increase in a cisplatin concentration. These results show that cisplatin has toxicity of debilitating cells.

On the other hand, FIG. 6C shows a relationship between a cisplatin concentration and the number of isolated structures. While the number of multiple isolated structures is counted in the group without administered cisplatin, the number of isolated structures increases significantly as a cisplatin concentration increases. The nephrotoxic properties of cisplatin are known to cause disorder and cutting of a part called a proximal tubule of a nephron. Also in such a kidney-like structure, the group with administered cisplatin was confirmed to have tendency toward progress of fragmentation. Namely, a result showing increase in the number of isolated structures indicates the nephrotoxic properties of cisplatin.

As described above, in the test of the toxicity of cisplatin on a kidney-like structure, both reduction in the volume or surface area of the kidney-like structure and increase in the number of isolated structures as index values determined based on OCT imaging data show that cisplatin has nephrotoxic properties. Thus, each of these index values can be used alone as a material for determining the presence or absence of toxicity. However, the presence or absence of toxicity is desirably determined comprehensively using a combination of these index values. The reason for this is that, even if toxicity causes progress of fragmentation of a tissue, a volume or surface area does not exhibit significant change in some cases. Regarding a surface area, in particular, a value is even increased by fragmentation of a tissue in some cases.

In the toxicity test described above as one mode of use of an OCT imaging result, displaying the image acquired by the imaging is not an absolute necessity. However, displaying the captured image of the three-dimensional cell-based structure is useful for the convenience of a user. In this case, in addition to displaying an image acquired by tomography, a stereoscopic image (3D image) reconstructed from multiple tomographic images, etc., an image may be displayed as follows, for example.

Figure 7:
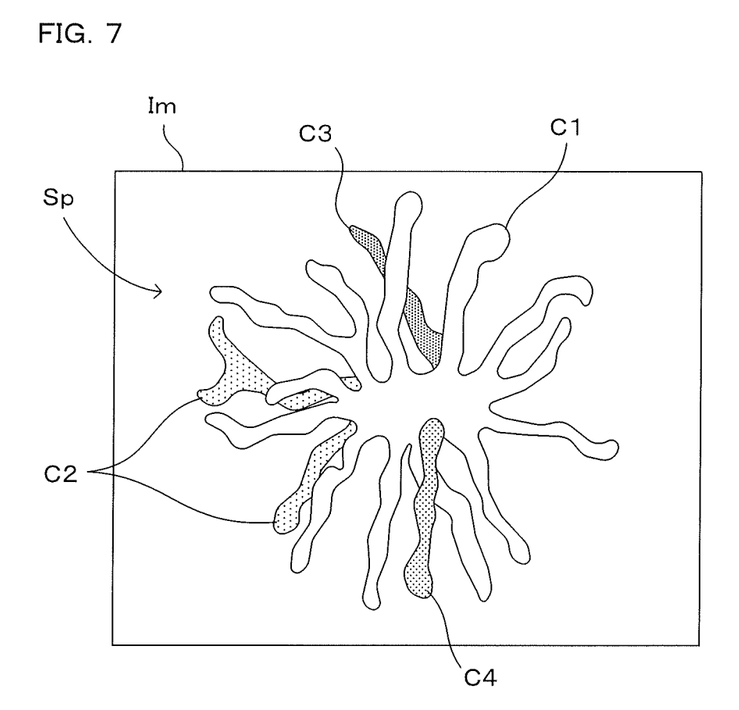
FIG. 7 schematically shows an example of display of the three-dimensional cell-based structure.

FIG. 7 schematically shows an example of display of the three-dimensional cell-based structure. As described above, in stereoscopic data generated from OCT imaging data, structures in the three-dimensional cell-based structure isolated from each other are handled as individual objects. Thus, by performing image processing in different ways on the objects, structures isolated from each other in actual imaging space but overlapping each other and thus regarded as a unity in the displayed image can be displayed in a manner in which the structures can be distinguished visually.

In the example of the displayed image Im shown in FIG. 7, multiple structures C1, C2, C3, and C4 overlapping in the image but actually isolated from each other are hatched in different ways. This allow a user to easily know that these structures are not connected but are isolated from each other in the three-dimensional cell-based structure. Here, for the convenience of description, the structures are distinguished by the way of hatching. However, in an actual displayed image, the isolated structures can be distinguished by being colored in different ways, for example.

As described above, in the embodiment, the number of structures isolated from each other in the three-dimensional cell-based structure is used as one index value for evaluating the state of the cultured three-dimensional cell-based structure. The number of these isolated structures shows a degree of progress of fragmentation of the tissue and functions as an index quantitatively indicating the state of the three-dimensional cell-based structure. The number of the isolated structures is an index value that can be calculated based on data acquired by OCT tomography and can be acquired noninvasively without damaging the three-dimensional cell-based structure to be evaluated. For these reason, the index value is used suitably for evaluating temporal change in the three-dimensional cell-based structure and used preferably for evaluating the medicinal effect of a chemical on the three-dimensional cell-based structure, for example. More specifically, the index value is usable in a toxicity test for examining the toxicity of the chemical to the three-dimensional cell-based structure, for example.

The present invention is not limited to the foregoing embodiment but may be changed in various ways in addition to the foregoing within a range not deviating from the substance of the invention. For example, in the foregoing embodiment, the idea of the present invention is applied to the test of the toxicity of the chemical to the particular three-dimensional cell-based structure. However, the three-dimensional cell-based structure to be evaluated is not limited to the foregoing but any three-dimensional cell-based structure can be evaluated. In particular, the idea of the present invention is effective in a three-dimensional cell-based structure having a complicated configuration with multiway branches, like the foregoing kidney-like structure.

The specimen in the foregoing embodiment is the structure like the tissue differentiated by culture from the stem cells. However, a three-dimensional cell-based structure to which the present invention is applied is not limited this. Also included in an object to be evaluated according to the present invention may be materials prepared by culture from cells or tissues retrieved from biological bodies, spherical cell aggregates (spheres), and structures (organoids) like organs prepared from various types of cells. Imaging by means of OCT does not require particular processing on a specimen for imaging, so that such three-dimensional cell-based structures resulting from various types of sources can be used as objects.

Purpose of evaluation is not limited to the toxicity test. The present invention is further applicable to evaluation of a culture condition for culturing a three-dimensional cell-based structure such as a type of a culture medium or temperature or humidity environment, and evaluation of influence of a chemical on a tissue with a lesion, for example. The present invention is further applicable to the purpose of evaluating the state of a three-dimensional cell-based structure simply without administering a chemical. In this case, while increase in the number of isolated structures is used as the index value about the toxicity of the chemical in the foregoing embodiment, the meaning of the counted number of isolated structures may be changed by the purpose of evaluation.

In the foregoing embodiment, the image processing apparatus 1 serving as the OCT imaging device further functions to evaluate the state of a three-dimensional cell-based structure in a captured image. As described above, however, a member for imaging and a member for image processing and evaluation based on imaging data may be different devices. Further, an imaging method for tomography is not limited to OCT. An imaging method based on other imaging principles is still usable for making the foregoing evaluation based on data acquired by this imaging method.

In the foregoing embodiment, the three-dimensional cell-based structure is evaluated only based on data acquired by OCT imaging. Alternatively, the three-dimensional cell-based structure may be evaluated using a combination of the acquired data and a result acquired by different experiment conducted using an appropriate reagent, for example.

As described above by giving the specific exemplary embodiment, the method of evaluating the three-dimensional cell-based structure according to the present invention may be configured in such a manner that a spatial region surrounded by a closed surface having spatial connectivity is counted as one structure identified in stereoscopic data. This spatial region can be identified by appropriate image processing of extracting a region having connectivity from an image. While a part of a three-dimensional cell-based structure having connectivity is handled as one structure, parts not continuous but isolated from each other spatially are handled as different structures. This makes it possible to count the number of structures forming the three-dimensional cell-based structure correctly.

Tomography may be performed using optical coherent tomography (OCT) technique. This imaging technique allows imaging of a cross-sectional configuration of the three-dimensional cell-based structure. This makes it possible to acquire information sufficient for generating stereoscopic data about the three-dimensional cell-based structure, even if the three-dimensional cell-based structure has a convoluted configuration. Thus, by using image data resulting from OCT imaging in the evaluation according to the present invention, quantitative evaluation of the three-dimensional cell-based structure can be made with high accuracy.

Tomography may be performed several times at time intervals, and a count may be made for each stereoscopic data resulting from corresponding imaging. This configuration achieves evaluation of temporal change in the state of the same three-dimensional cell-based structure. According to the present invention, noninvasive imaging and evaluation based on a result of the imaging are combined to avoid damage on a three-dimensional cell-based structure to be caused by the work for the evaluation. In this way, the same specimen can be observed and evaluated continuously.

In the medicinal effect evaluation method according to the present invention, at least one of the total area and total volume of structures may be calculated based on stereoscopic data, and the medicinal effect of a chemical may be determined based on a result of the calculation and a result of the count of structures. In this way, the evaluation is made comprehensively based on multiple indexes to allow increase in the accuracy of the evaluation to a higher level.

While the invention has been described in line with the specific embodiment, the description is not intended for interpretation of the invention in a limited sense. By referring to the description of the invention, various modifications of the disclosed embodiment will become apparent to a person having through knowledge of this technique, like other embodiments of the present invention. Thus, the scope of the accompanying claims is regarded as covering such modifications or embodiments within a range not deviating from the true range of the invention.

INDUSTRIAL APPLICABILITY

The present invention is applicable to the purpose of examining the effect of a chemical on a cultured three-dimensional cell-based structure and useful in drug design of developing a medicine to act effectively in a biological body, for example.

REFERENCE SIGNS LIST 1 image processing apparatus
10 holder
20 imaging unit
21 light source
22 beam splitter
24 objective optical system
26 photo-detector
30 control unit
33 signal processor
34 3D restoration section
352 display section
Sp specimen

The invention claimed is:

1. A method of evaluating a three-dimensional cell-based structure comprising:
   performing tomography of a cultured three-dimensional cell-based structure, the three-dimensional cell-based structure formed from a plurality of isolated structures;
   generating stereoscopic data indicating the three-dimensional shape of the three-dimensional cell-based structure based on image data acquired by the tomography; and
   separating the isolated structures from each other in the three-dimensional cell-based structure based on the stereoscopic data and counting a number of the isolated structures.

2. The evaluation method according to claim 1, wherein a spatial region surrounded by a closed surface having spatial connectivity is counted as one isolated structure identified in the stereoscopic data.

3. The evaluation method according to claim 1, wherein the tomography is performed using optical coherent tomography technique.

4. The evaluation method according to claim 1, wherein the tomography is performed several times at time intervals, and the count is made for each stereoscopic data resulting from corresponding imaging.

5. A method of evaluating medicinal effects of a chemical, the method comprising:
   administering the chemical to be evaluated to a cultured three-dimensional cell-based structure;
   evaluating the three-dimensional cell-based structure with the administered chemical using the evaluation method according to claim 1; and
   determining the medicinal effects of the chemical on the three-dimensional cell-based structure based on a result of the evaluation of the three-dimensional cell-based structure.

6. The method according to claim 5, wherein at least one of the total area and total volume of the isolated structures is calculated based on stereoscopic data, and the medicinal effect of a chemical is determined based on a result of the calculation and a result of the count of the isolated structures.

7. The evaluation method according to claim 2, wherein the tomography is performed using optical coherent tomography technique.

* * * * *